US007283857B1

(12) United States Patent
Fallon et al.

(10) Patent No.: US 7,283,857 B1
(45) Date of Patent: Oct. 16, 2007

(54) DICOM COMPLIANT FILE COMMUNICATION INCLUDING QUANTITATIVE AND IMAGE DATA

(75) Inventors: John P. Fallon, Andover, MA (US); Howard P. Weiss, Newton, MA (US); David Mislan, Lexington, MA (US)

(73) Assignee: Hologic, Inc., Bedford, MA (US)

( * ) Notice: Subject to any disclaimer, the term of this patent is extended or adjusted under 35 U.S.C. 154(b) by 0 days.

(21) Appl. No.: 09/449,002

(22) Filed: Nov. 24, 1999

Related U.S. Application Data (60) Provisional application No. 60/110,210, filed on Nov. 30, 1998.

(51) Int. Cl.
*A61B 5/00* (2006.01)

(52) U.S. Cl. .................. 600/407; 707/100; 707/104.1; 128/920

(58) Field of Classification Search ............... 600/300, 600/407, 425; 128/920; 378/62–65; 345/424; 707/100, 104.1; 715/500, 500.1, 505, 507, 715/513, 700
See application file for complete search history.

(56) References Cited

U.S. PATENT DOCUMENTS 5,654,555 A * 8/1997 Buytaert et al. ............ 250/581
5,655,084 A * 8/1997 Pinsky et al. ............... 395/203
5,950,207 A 9/1999 Mortimore et al.
5,971,923 A 10/1999 Finger
5,986,662 A * 11/1999 Argiro et al. ............... 345/424

OTHER PUBLICATIONS

Crowe B, et al., Evaluation of Digital Chest Computed Radiology (CR) Unit and Image Distribution System at the Prince Charles Hospital Brisbane, Australia, Medical Technology Symposium, 1998, IEEE Comput. Soc, US, pp. 240-243.

Azancot I, et al., Electronic Image Archiving in the Catherterization Laboratory: Multicenter Comparison of Enhanced Optical Storage with 1024 Digital and 35 mm cine-film, Computers in Cardiology, 1996, pp. 121-124.

\* cited by examiner

*Primary Examiner*—Ruth S. Smith
(74) *Attorney, Agent, or Firm*—Cooper & Dunham LLP (57) ABSTRACT

A method of generating medical information including quantitative and image data, comprising steps of performing an image acquisition of at least a portion of a patient to be examined, generating image data based on the performed acquisition, generating quantitative data based on the performed acquisition and constructing a DICOM compatible file, the image data being provided in an image data field and the quantitative data being provided in another field of the DICOM compatible file.

16 Claims, 12 Drawing Sheets

| Scan Type | Report Types | | |
|---|---|---|---|
| | Most Recent Value | Rate of Change | Stand BMD |
| Spine | Y | Y | Y |
| Hip | Y | Y | Y |
| Forearm | Y | Y | |
| Lateral Spine | Y | Y | |
| AP/Lateral Spine | Y | Y | |
| Whole Body | Y | Y | |

FIG. 10

DICOM COMPLIANT FILE COMMUNICATION INCLUDING QUANTITATIVE AND IMAGE DATA

REFERENCE TO RELATED APPLICATION

This application claims the benefit of provisional Application Ser. No. 60/110,210, filed Nov. 30, 1998, which is herein incorporated by reference.

FIELD

The present disclosure relates to the communication of medical information where the medical information includes both images and corresponding quantitative data. More specifically, the present invention relates to the communication of both image and quantitative medical information using the DICOM standard.

DESCRIPTION OF THE RELATED ART

In a conventional radiology workflow, an operator enters patient and demographic information (such as patient name, age, referring physician, imaging device etc.) using the operator interface of the imaging device. The operator then performs an image acquisition. The resulting images are acquired on film or are printed onto a film. If the patient has had previous image scans performed, the patient's film folder may be pulled from the patient file room and the new film added to the folder. The patient film folder with the new and old scans can then delivered to the radiologist in a reading room. The radiologist views the images and dictates a report. The report often includes the data from the scan. The patient film folder is then returned to the file room and the radiologist's report is sent to the referring physician. However, this process is inefficient and prone to human error. In addition to the use of a traditional paper medical chart/report, film scan, etc. being inherently inefficient, requiring staff members to waste valuable time locating a chart, film jacket schedule, etc., a film scan or report can easily be filed in the wrong patient folder or not filed in the correct location in the film/storage room. In addition, only one individual may view the file at any one time.

Health care providers today are faced with the task of reducing costs. One method of reducing health care costs is the use of electronic medical charts, images, etc.

Using electronic medical charts/images has several advantages over using paper or film copies. First, the possibility of filing an electronic patient chart or film scan in the wrong location is virtually eliminated because patient information and the scanned images can be included in a single image file. Second, the electronic information is easily transmitted from one location to other locations within the medical facility or even to a remote location. Third, multiple users may access the information simultaneously. Fourth, the archiving/retrieval process is much faster and accurate when medical imaging information is stored in electronic form. Finally, the electronic form of medical charts/images leads to faster interpretation and quicker turnaround time because the information is available to the physician within moments of it being requested or generated, thus resulting in a faster response to the referring physician and patient and a shorter billing cycle.

The Digital Image Communication in Medicine (DICOM) standard was developed to facilitate the communication of medical images in electronic form. The DICOM standard is a collection of detailed specifications that describe a system of formatting and exchanging medical images and associated information on a computer network. The standard applies to the operation of the interface used to transfer data in and out of a conforming device. DICOM relies on computer industry standard network connections, and media devices that address the communication and storage of digital images from diagnostic devices such as CT, MR, PET, Nuclear Medicine, Ultrasound, X-ray, CR, digitized film and video capture information. It also supports the connection of networked printers, such as laser imaging devices. As long as electronic medical records and images are DICOM-Compliant, a medical facility will be capable of receiving the DICOM-formatted images from multiple sources and departments.

The DICOM standard enables medical imaging devices to generate image files which can interface with other devices on a DICOM network. An operator acquires patient demographic information either by entering it at or by downloading it to the imaging device and then performs an image acquisition. The imaging device generates a DICOM conformant file; the file contains demographic information, information about the image, and the image. The file can then be sent to other devices on the medical facility's DICOM network. These devices include DICOM viewing stations, printers or archiving systems such as PACS (Picture Archiving and Communications Systems). In addition, the DICOM file can also be readily available at critical points in the hospital such as operating rooms and critical care units.

The DICOM standard has become the predominant standard for the communication of medical images generated by a typical medical imaging device. However, the existing DICOM standard does not accommodate medical information of the type generated by bone densitometers. For example, a typical medical imaging device generates an image or a series of images. The physician then uses these images to make a diagnosis. On the other hand, a bone densitometer generates quantitative data (e.g., bone mineral density (BMD) values or quantitative morphometry) in addition to the scanned image. A physician typically makes a diagnosis by comparing the BMD values with reference data (age, sex and ethnicity matched). The physician may also view the image to ensure technical quality of the data acquisition and analysis process. The physician's diagnosis is typically based on both the BMD values and the scanned image.

The current DICOM standard does include a category of devices called "Secondary Capture Devices". A typical "Secondary Capture Device" would be a digital camera or a film scanner. However, a "Secondary Capture Device" would also be deficient in communicating necessary bone densitometer information in the following ways:

(1) A "Secondary Capture Device" does not encode the information needed to interpret the scan;

(2) A "Secondary Capture Device" does not preserve the fidelity of the scanned image;

(3) A "Secondary Capture Device" does not produce information needed to construct a digital report; and (4) The "Secondary Capture Device" does not produce information needed to enter results into a database.

The current DICOM standard does not address the communication of medical information of the type generated by such bone densitometers. That is, the DICOM standard does not address the electronic communication of both image and quantitative data.

Accordingly, a need exists for a method of communicating the type of medical information generated by a bone densitometer including both image and quantitative data in a form that complies with the DICOM standard.

SUMMARY OF THE INVENTION

A method is disclosed for generating medical information including quantitative and image data. The method comprises steps of performing a scan of a patient to be scanned, generating image data based on the performed scan and generating quantitative data based on the performed scan. A DICOM compatible file is then constructed, the image data being provided in an image data field and the quantitative data being provided in another field, e.g., the Image Comments field, of the DICOM compatible file. The scan can be performed and the image data generated using a bone densitometer. The quantitative data may comprise bone mineral density (BMD) data and/or quantitative report data, wherein the quantitative report data may comprise BMD data, T scores and Z scores. The image data may comprise an image of the patient's anatomy which was scanned. The quantitative data provided in the image comments field may be in the form of HTML, XML or Java Script files. The method may further comprise steps of communicating the DICOM compatible file across a network, receiving the DICOM compatible file at a DICOM complaint station, extracting the quantitative data from the image comments field of the DICOM compatible file and generating a report using the extracted quantitative data. The extracting step can be performed using a software component such as the Hologic® Active X Control™ customized interface. The quantitative data can include raw According to another aspect, a method is provided for generating a DICOM file including embedded quantitative data. The method comprising generating a report image file, embedding the report image file as an image file portion of the DICOM file and embedding the quantitative data, used to create the report image file, in another field of the DICOM file. The report image file may comprise a bitmap image file. The quantitative data used to create the report image file may comprise raw data. The quantitative data used to create the report image file may comprise bone mineral density (BMD) data.

According to still another aspect, a computer executable software code is stored on a computer readable medium, the code for creating a DICOM compliant file. The code comprises code for creating a report, including quantitative data, from scan data generated by an image capture device, code for creating a bitmap image file representing the created report, code for embedding the bitmap image file in an image field of a DICOM compliant file and code for embedding the quantitative data in an image comments field of the DICOM compliant file. The quantitative data may comprise raw data used to create the report. The quantitative data may comprise bone mineral density (BMD) data.

The present system is superior to a "Secondary Capture Device" in at least the following ways:

(1) The present system embeds quantitative analysis data directly in the image in the generated DICOM file, thus providing a physician with all information necessary to interpret a bone mineral scan visually.

(2) The present system directly converts the image information pixel by pixel when is constructs the DICOM report, thus preserving the physical and densitometric resolution of the image.

(3) The present system embeds all information necessary to generate a digital report in the Image Comments section of the DICOM file so that a computer can reconstruct a digital report similar to the original QDR report.

(4) The present system allows a computer to extract necessary identifying and result information to construct a database of received scans.

The present invention can be used for any modality with image, graphic, and quantitative results to be exported.

DETAILED DESCRIPTION OF THE PREFERRED EMBODIMENTS

The present disclosure describes a software system which enables a device such as a bone densitometer device, which generates quantitative data in addition to image and/or graphic data, to interconnect with other medical devices on a DICOM network. Though the present description relates to the communication of information between bone densitometers and other DICOM devices, the present invention is not limited thereto and the present description is intended to encompass communication between any medical imaging device that generates quantitative and image data with other devices on a DICOM network.

A system according to an embodiment of the present invention encapsulates and transmits the quantitative information and image information generated by a bone densitometer, for example, in a format easily usable by physicians for interpretation and diagnosis. In addition, the system provides the information in computer readable form so that the quantitative information may be stored in a database for archiving and retrieval purposes or reconstructed in a report or series of reports.

The present disclosure describes a unique method for the generation of a composite image file. A bone densitometer device such as a QDR (Quantitative Digital Radiography) 4000 series device manufactured by Hologic, Inc., performs a scan on a patient and generates quantitative data including BMD data and bone mineral content (BMC) data. The QDR device can also calculate T and Z scores, can graph BMD data verses reference data, etc. This is in addition to generating an image of the scanned body part. The quantitative data can be displayed or printed at the QDR device as a report. According to an embodiment of the present invention, a composite DICOM compatible image file is generated which contains the BMD data, T and Z scores, a graph of BMD versus reference data and an image indicating the scanned portion of the patient's anatomy. The file also includes scan and modality specific information such as the date and time of scan, type of scanning device and analysis algorithm. The generated composite image file is DICOM compatible and provides all the information required by a physician to perform a complete and accurate diagnosis.

Figure 1A:
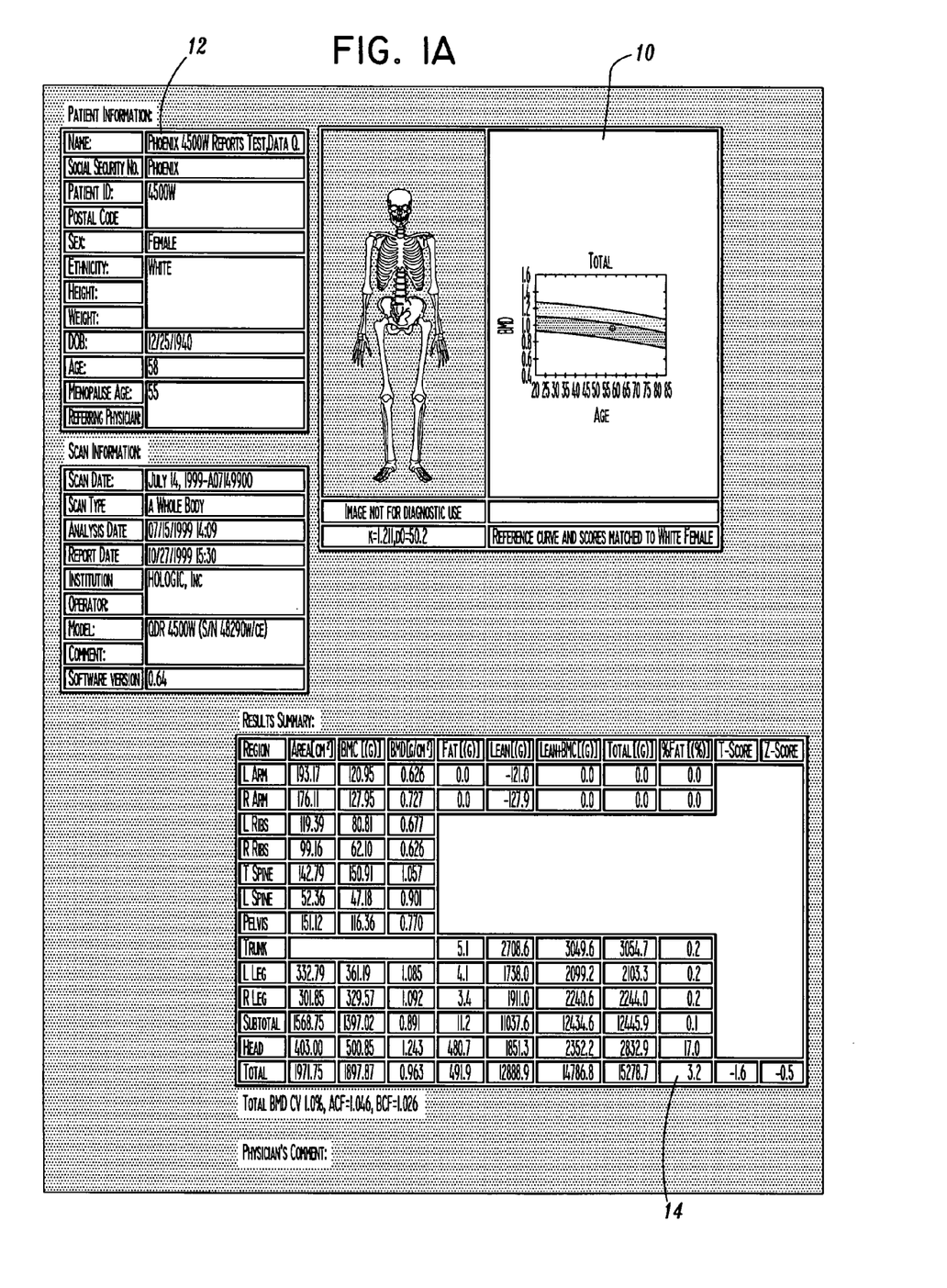
FIGS. 1A and 1B show a whole body scan and a body part scan, respectively, including reports produced on a QDR type bone densitometer.
Figure 1B:
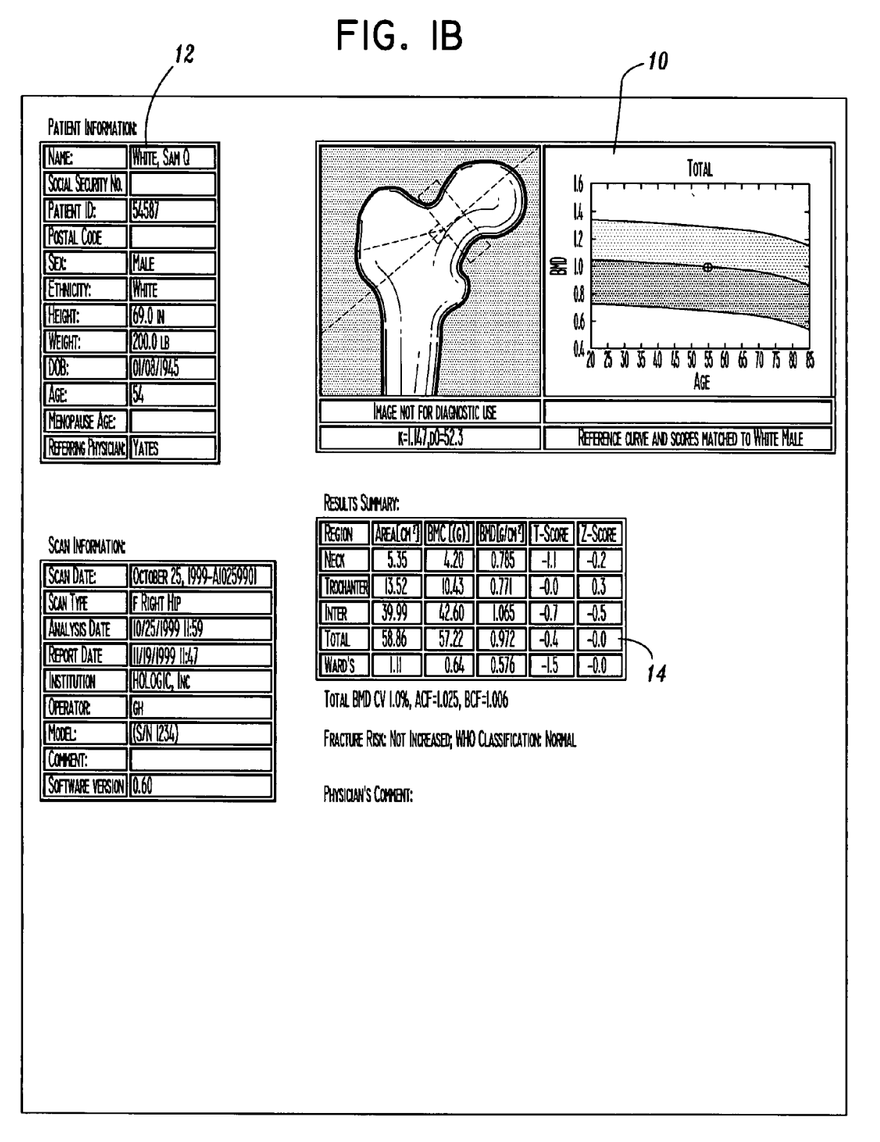
Figure 2A:
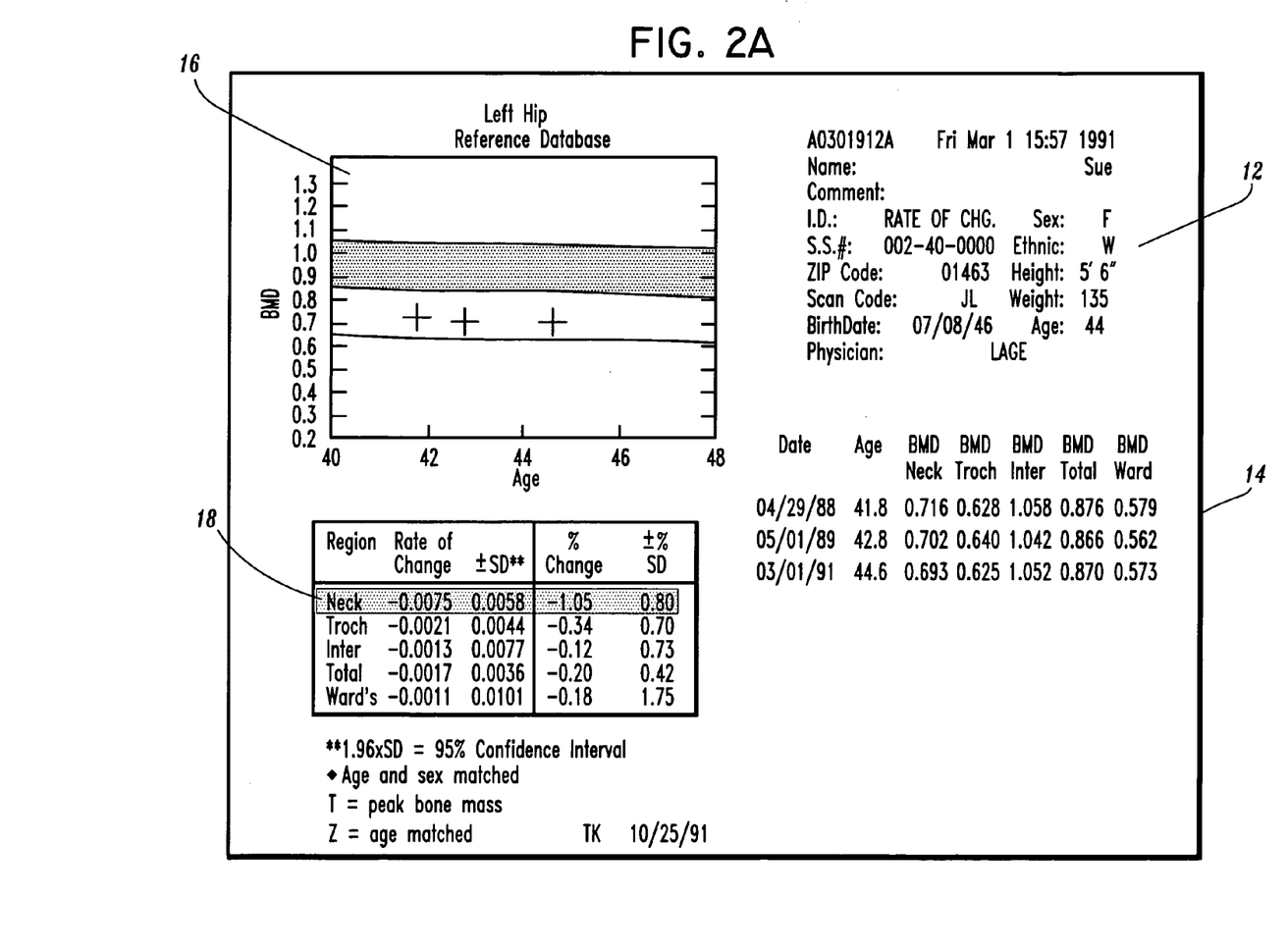
FIGS. 2A and 2B depict different types of plots, including a rate of change plot and a reference plot, capable of being produced on a QDR type bone densitometer.
Figure 2B:
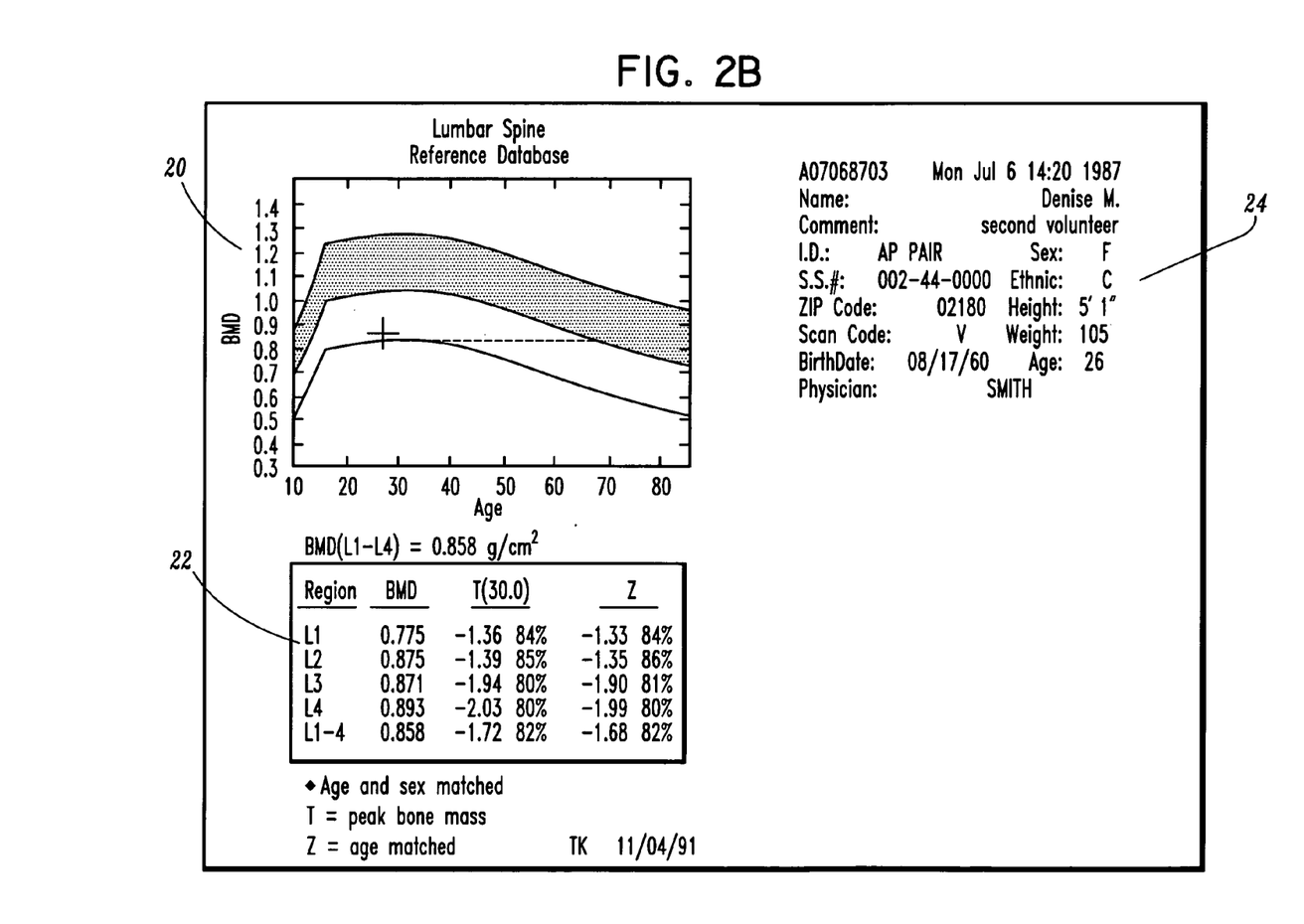

Examples of the types of reports that are generated by a QDR device are shown in FIGS. 1 and 2. As shown in FIG. 1A, a whole body image acquisition or scan can be performed and displayed along with the report which can include an image of the body 10 as well as quantitative data 14 and patient demographic data 12. In the alternative, a partial body image acquisition or scan can be performed as shown in FIG. 1B. As shown in FIG. 2, a report can also consist of a rate of change report such as that shown in FIG. 2A, including a graph 16 showing bone mineral density versus age, a graph 18 showing the annualized rate of change of BMD for the patient, as well as other quantitative data 14 and patient demographic data 12. As shown in FIG. 2B, the report can include a graph 20, T and Z scores chart 22 and demographics 12.

A number of vendors have developed standard software components which support authoring and display of web pages. These include layout tools (such as Microsoft Front Page) and components which render HTML and JavaScript on a screen (such as the Microsoft Web Browser Control) and/or render components of an image (such as the Lead Tools Graphics Display Control). The present invention employs these technologies for the generation of DICOM conformant files. An overview of a system for forming a DICOM conformant file according to an embodiment of the present invention is described with respect to FIG. 3.

Figure 3:
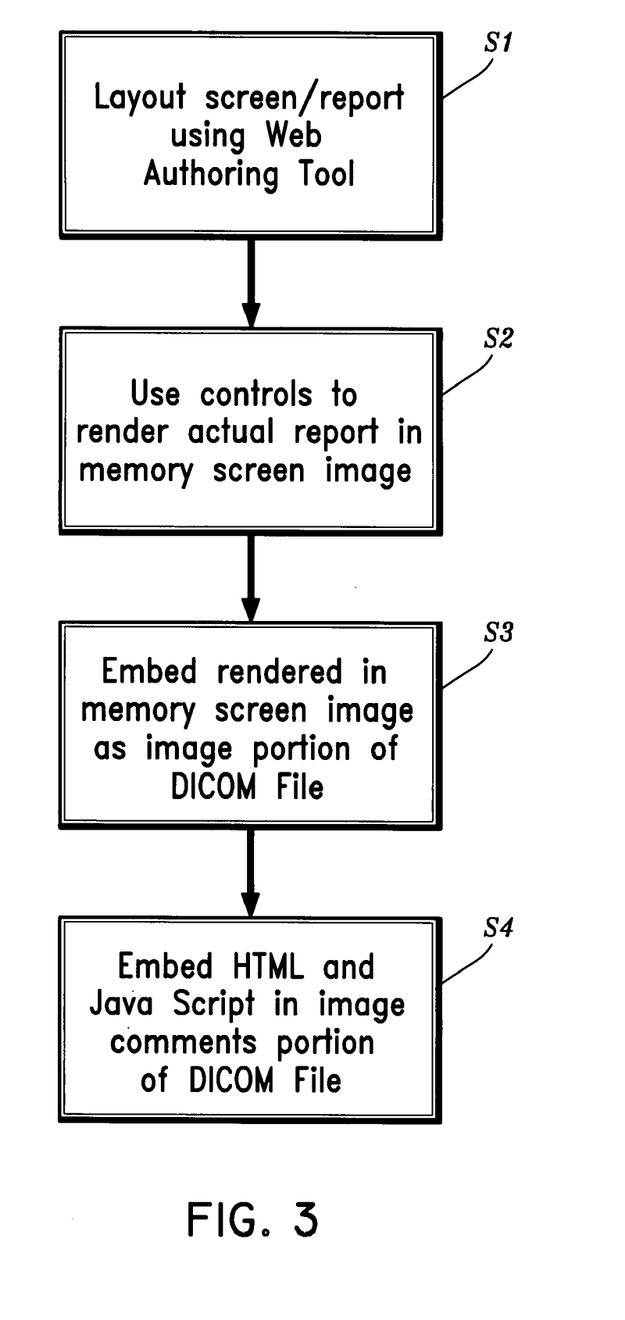
FIG. 3 is a flow chart for the generation of DICOM conformant files according to an embodiment of the present invention.

First, a screen/report is laid out using a Web authoring tool such as Microsoft Front Page (Step S1). A Web browser control such as Microsoft Web Browser Control is used to render the actual report to an in memory screen image (Step S2). Access to the scan specific data such as the quantitative results and scanner, patient and demographic information can be provided. The rendered in memory screen image is then embedded as the image portion of the DICOM file (Step S3). HTML and JavaScript files are embedded in the image comments field of the DICOM file (Step S4). These files provide a complete description of the report elements as they are encoded in the image, allowing for the extraction of graphic information such as the image or reference data graph. In addition, the system tags each datum e.g., BMD, reference score, patient and scanner demographics in a format such that it can be easily extracted. This facilitates the creation of custom reports and/or extraction of data for inclusion in a custom database.

Once the DICOM image is complete, it can be queued for transmission to a DICOM compliant device which has sufficient capability to receive DICOM images.

In addition, the DICOM file generated by the present invention allows the operator to either print the generated image on a local printer and/or save the generated DICOM file on the local hard disk.

Figure 4:
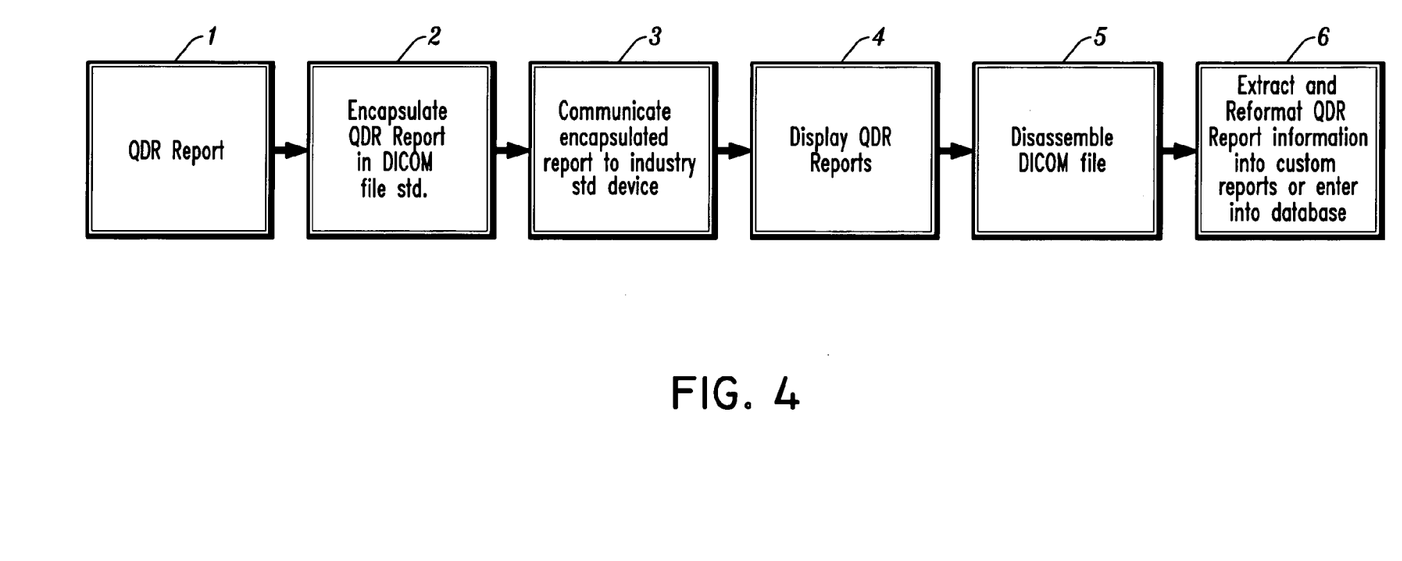
FIG. 4 shows the flow of encapsulation and extraction according to an embodiment of the present invention.

The present invention is useful for several reasons. For example, as described above and as shown in FIG. 4, the present invention QDR DICOM options allow for the encapsulation of a QDR report 1 in an industry standard format 2 which can be communicated to industry standard viewing, archiving, and/or hardcopy devices 3. Physicians can use, receive and review the DICOM files and view QDR reports at radiologic workstations 4. In addition, the QDR DICOM file may be disassembled 5 and the components of the QDR results can be extracted and reformatted into custom reports and/or entered into a database 6.

Access to the data embedded in the Image Comments section of the DICOM file is readily available to a programmer familiar with HTML and Java. It may also be made available through a customized software interface, such as Hologic® Active X Control™ customized interface. The information is also directly accessible and can be written to a database such as Microsoft's Access.

Once the DICOM file is generated, the file may be transmitted over the facility's network to the physician's DICOM viewing station either within the facility or at a remote location. The file can be read immediately or it can be queued for later reading. In addition, the report can be archived in the same way as images produced by other modalities (i.e. CT scanner) and can be made available subsequently via query/retrieve for patient follow-up. Each time a patient returns for a follow-up scan, prior analysis reports are immediately available on-line for comparison.

An advantage of the present system is that it provides all the information a physician will need to interpret the scan, in electronic form. As stated above, information in electronic form has many advantages over information on film or paper chart form, for example. Another advantage of the present system is easy and convenient access to data in computer readable form. This capability facilitates manipulation of data in digital form. The data can easily be stored in a database, and calculations can easily be performed once the data is in the database. Because data is directly transferred from the imaging device into a database, any errors resulting from human data entry are eliminated.

Figure 6:
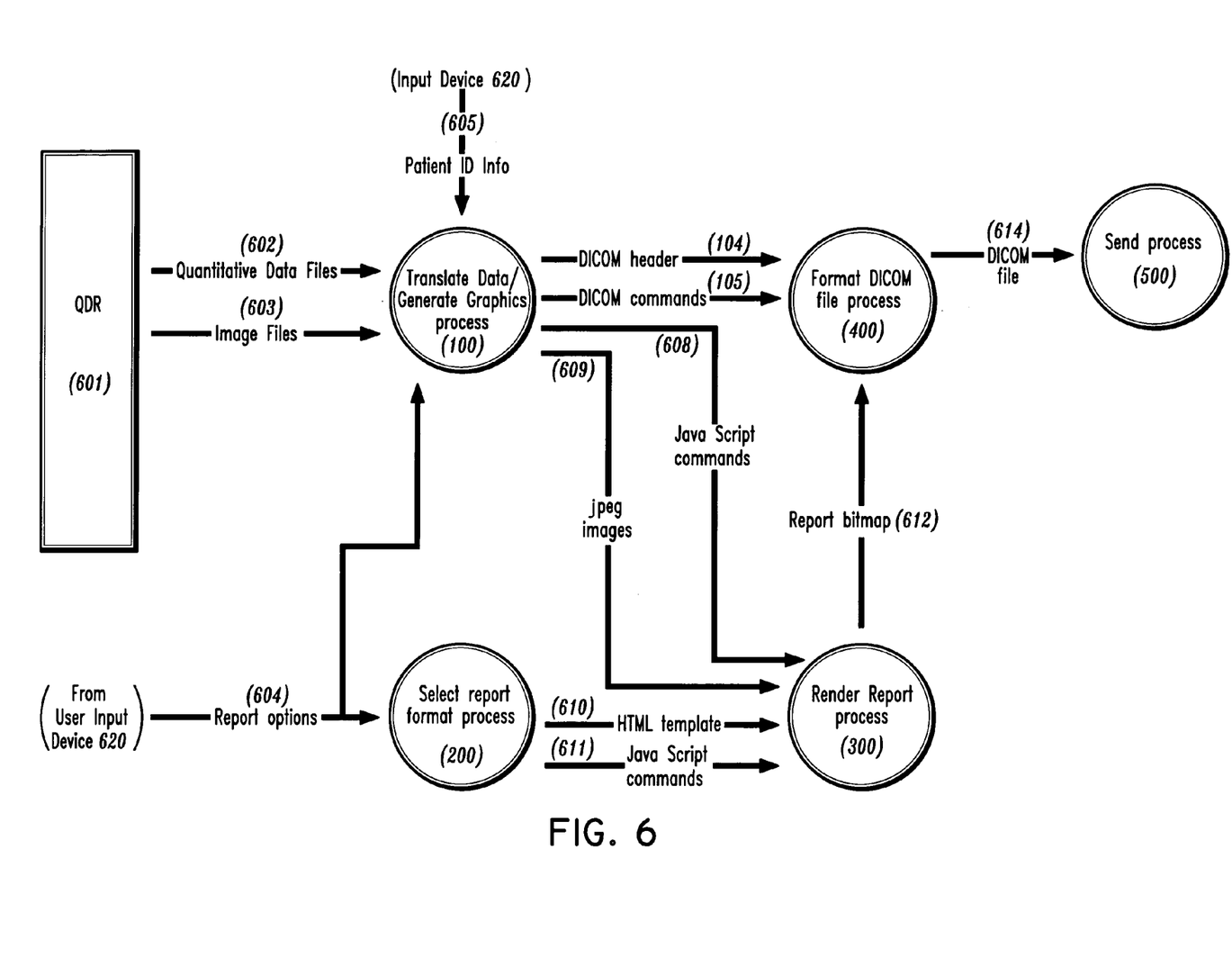
FIG. 6 shows a more detailed flow of a process of generating a DICOM file according to an embodiment of the present invention.

FIG. 6 shows a more detailed flowchart of an encapsulation process for forming a DICOM compliant file according to an embodiment of the present invention, including quantitative data and image data. The system shown in FIG. 6 includes five main processes. QDR device 601 represents a type of bone densitometry device that generates quantitative data as well is image data for use by a physician during patient analysis. The processes described herein can be performed in the QDR device 601 itself or can be performed in a separate processing system (e.g., a PC) interfacing with QDR 601. The quantitative data is stored in quantitative data files 602 and the image data is stored in image files 603.

Translate Data/Generate Graphics Process 100 receives information from quantitative data files 602 and image files 603 generated by QDR device 601. Process 100 also receives user input information including selected Report Options information 604 and Patient Identification information 605. Patient Identification information 605 may include an Accession number, for example. Process 100 generates DICOM Header 104, DICOM commands 104, Java Script commands 608 and JPEG Images 609 for use by other processes as will be described below.

Select Report Format Process 200 also receives selected Report Option information 604 and provides a HTML Template 610 and Java Script Commands 611 to Render Report Process 300.

Render Report Process 300 receives the Java Script Commands 608 and JPEG Images 609 from Process 100 and the Java Script Commands 611 and HTML Template 610 from Process 200 and renders a Report Bitmap 612 based thereon. Format DICOM File Process 400 receives the Report Bitmap 612 from Process 300 as well as DICOM header 104 and DICOM Commands 105 from Process 100 and formats the information into an appropriate DICOM file 614. The DICOM file 614 can then be transferred using an ordinary DICOM file transfer protocol via Send Process 500.

Figure 7:
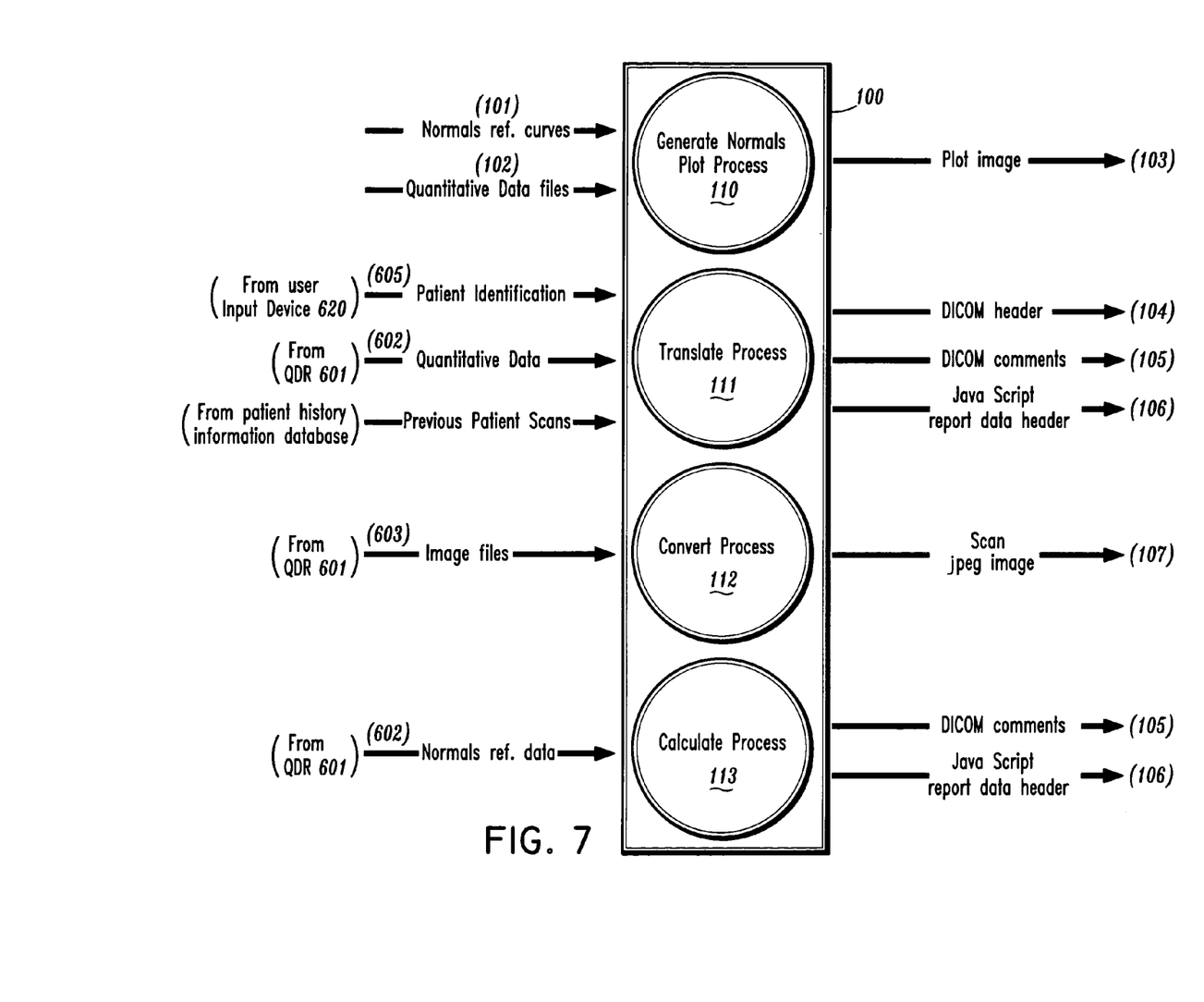
FIG. 7 is a more detailed flow chart of the Translate Data/Generate Graphics Process shown in FIG. 6.

As shown in more detail in FIG. 7, Translate Data/ Generate Graphics Process 100 can be divided into four separate Processes 110-113. Generate Normals Plot Process 110 processes data including quantitative curve file data 102 for the patient being tested and Normals reference curves data 101 provided from a reference database (not shown) which specify "normal" BMD and standard deviations as a function of age, for example. (e.g., see graph 20, FIG. 2B) The quantitative curve file data 102 can be stored in and retrieved from quantitative data files 602. A plot image of the Normals data and Patient data is output as JPEG image 103.

Translate process 111 receives the Patient Identification Information 605 input from user input 620, quantitative data 602 from the QDR 601 and can also process the patient's history of scans input from a patient history information database (not shown) to produce a Rate of Change report such as that shown in FIG. 2A. The patient history information database and the reference database can be stored in QDR 601 or on a separate storage medium (not shown). Translate Process 111 processes and translates the provided data to generate a DICOM header 104, DICOM comments 105 and Java Script Report Data Header 106.

Convert Process 112 converts the image files 603 from QDR 601 into a Scan JPEG Image 107.

Calculate Process 113 receives Normals Reference Data 602 from the reference database. The Normals Reference Data along with measured BMD values for the patient are used to calculate T and Z scores (see FIG. 2B) which are output as DICOM comments 105 and Java Script report data header 106.

Figure 8:
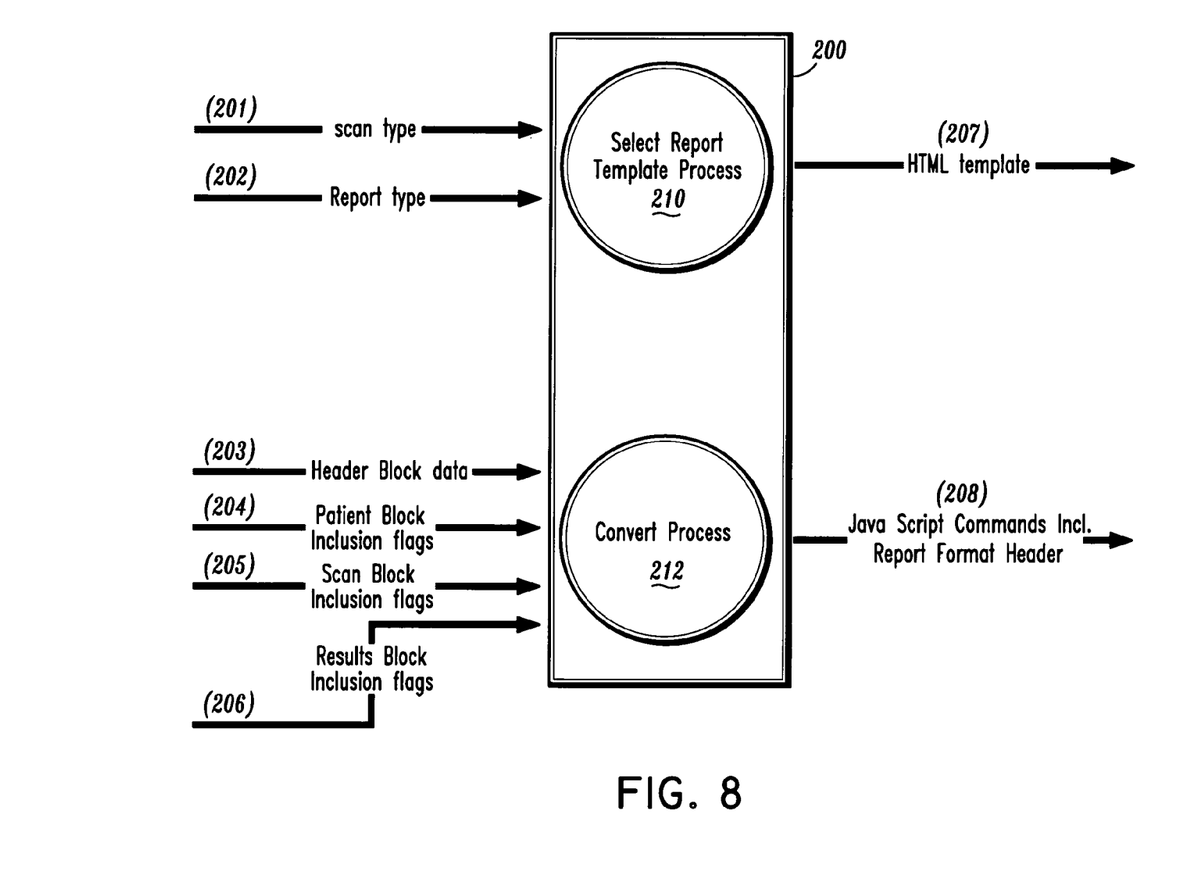
FIG. 8 is a more detailed flow chart of the Select Report Formal Process shown in FIG. 6.
Figure 10:
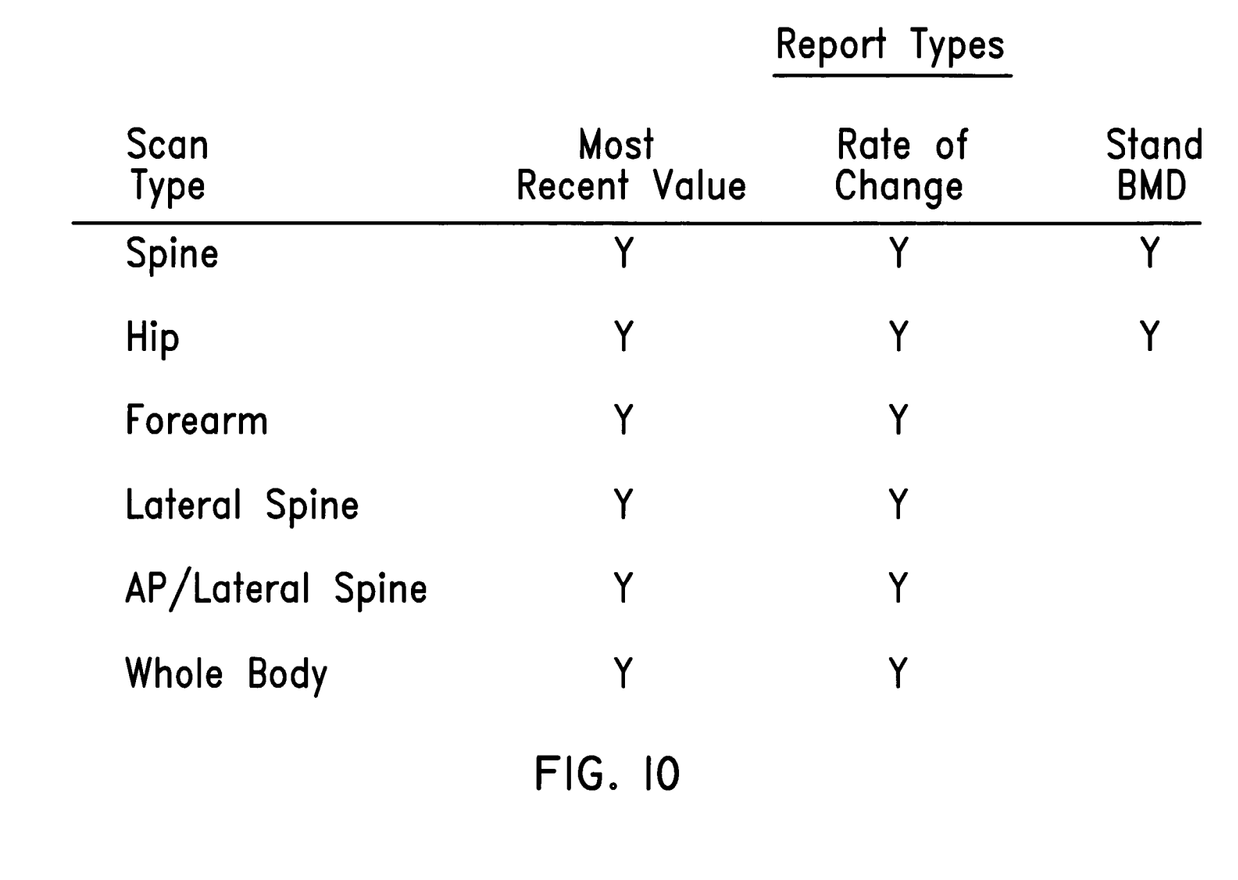
FIG. 10 shows the various report types available for different scan types according to an embodiment of the present invention.

As shown in FIG. 8, Select Report Format Process 200 can be divided into a Select Report Template Process 210 and a convert Process 212. Select Report Template Process 210 receives scan type information 201 which identifies the part of the body that was scanned. Select Report Template Process 210 also receives Report Type information 202 which identifies the type of report to be output. FIG. 10 shows the types of reports which can be generated for each type of scan. Based on the scan type and report type, an HTML report template 207 is selected and output from a database of templates.

Convert process 212 converts the header block data 203, patient block inclusion flags 204, scan block inclusion flags 205 and results block inclusion flags 206 into Java Script commands 208 including a report format header, based on the report options selected. Process 212 is a program that accepts the information shown and generates Java script commands which are interpreted by process 300 to render a bit mapped report. The inclusion flags allow the report to be configurable such that certain fields are included or excluded from the bit mapped report depending on the states of the flags. The inclusion flags are converted to Java script variables which specify which report fields are visible.

Figure 9:
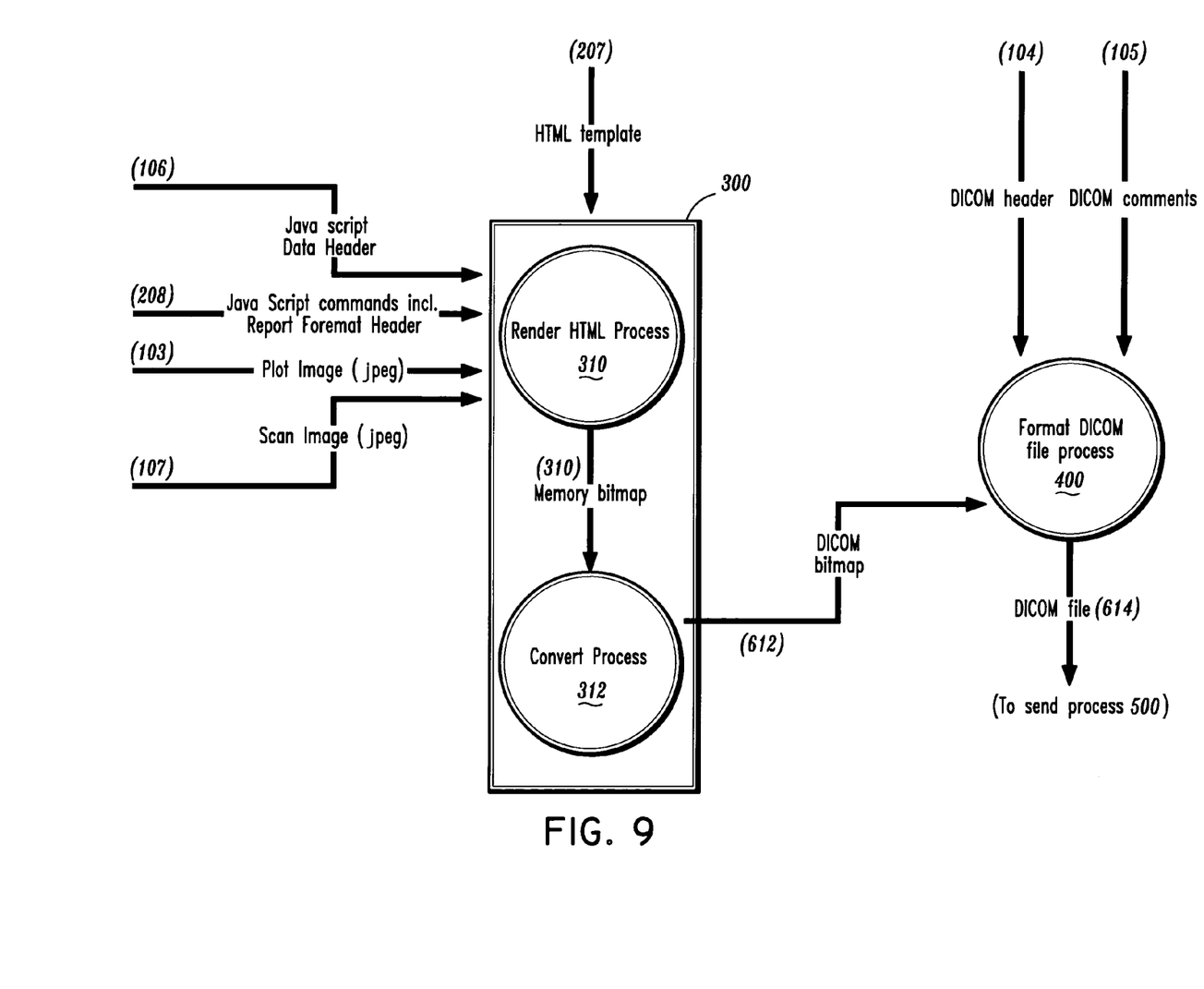
FIG. 9 is a more detailed flowchart of the Render Report Process shown in FIG. 6.

As shown, in FIG. 9, Render Report Process 300 can be divided into a Render HTML Process 310 and a Convert Process 312. Render HTML Process 310 receives the Java Script Data Header 106 from Processes 111 and 113, Java Script Commands including the Report Format Header 208 from Process 212, Plot JPEG image 103 from Process 110, the Scan JPEG image 107 from Process 112, and the HTML Template 207 from Process 210. Render HTML Process 310 performs HTML report rendering, generating Memory Bitmap data 301. Convert Process 312 then converts the Memory Bitmap data 301 into a DICOM Bitmap 612.

Figure 5:
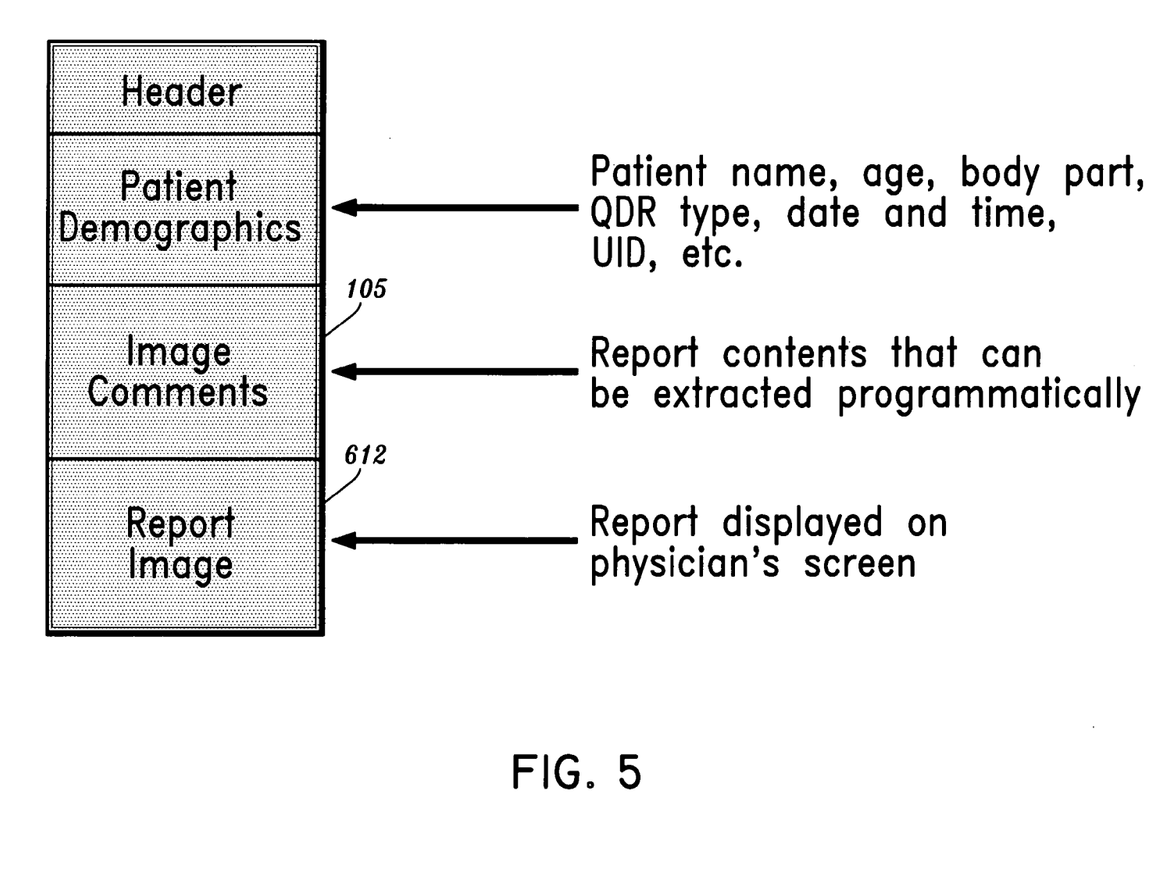
FIG. 5 shows the elements of a DICOM file according to an embodiment of the present invention.

Format DICOM File Process 400 receives the DICOM header 104 and DICOM comments from Process 100 and the DICOM bitmap 612 from Process 312 and formats the information into a DICOM File 614 such as that shown in FIG. 5. DICOM file 614 is then sent to Send Process 500 where it can be queued and sent out as a DICOM compliant data file.

As mentioned above, QDR device 601 can be a bone densitometer device such as a Hologic 4000 series bone densitometer, for example, which generates quantitative data (BMD values) and an image (a low resolution image of the scanned anatomy). The quantitative data is stored in quantitative data files 602. The image is stored in image files 603. When performing image acquisition, the operator may assign defined patient identification information or an accession number 605 for the patient via a user input device 620 such as a keyboard, mouse, etc. The user input device 620 may or may not be an input device associated with the QDR device 601. The patient identification 605 is uniquely associated with a patient and is typically generated by a Radiological Information System or a Hospital Information System.

The operator may also select report options 604 from an existing report options database also via a user input device 620. The Report options database can be a database of HTML templates generated using a standard Web authoring tool such as Microsoft Front Page. In one embodiment of the present invention the report may contain an image, a graph, a set of tables containing specific information on the patient, and the results of the analysis. The Report options database can include report templates to generate, for example, a Standard BMD Report, a Rate of Change Report and a Most Recent Value Report.

The Most Recent Value report can provide all the information necessary to interpret the scan. For example, the Most Recent Value report can provide quantitative results from a single scan and analysis including the scanned image and reference population curves.

The Rate of Change Report can include the Most Recent Values Report and may also include a comparison with previous scans, thus simplifying comparing visit-to-visit change. Significant changes can be noted on the report to facilitate clinical management.

The Standardized BMD Report generates a standard BMD report. A standard BMD report includes a scan image, calculated BMD data, and the reference population curves and values. The BMD data is calculated by performing operations on the scanned data and a comparison with reference data. The reference data is stored in a separate database. For example, to obtain calculated BMD data for the HIP, a predefined reference database must be installed and selected when performing the scan.

FIG. 5 shows a DICOM file structure generated according to the present invention. The DICOM file includes Patient Demographics including patient name, age, body part, QDR type, date and time of scan, etc. The Image Comments Field 105 includes the quantitative report content that can be extracted programmatically. Report Image Field 612 is the bitmap report image that is displayed on the screen.

The information embedded in the Image Comments Field 105 can be accessed by using, for example, the Hologic DICOM Interface™ software interface. The Hologic DICOM Interface™ software interface is capable of reading the Image Comments Field of the DICOM files and extracting the quantitative data. The information continued in the Image Comments Field may also be directly accessed or written to a database such as Microsoft Access.

The following files can be incorporated into the Image Comments Field of the DICOM file being generated:

Patient Information File

The Patient Information file is a JavaScript file that may contain the following information: Patient Name, SSN (Social Security Number), Patient ID, Patient Code, Patient Sex, Ethnicity, Height, Weight, DOB (Date of Birth), Age, Menopause Age, Referring Physician, etc.;

Scan Information File

The Scan Information file is a JavaScript file that may contain the following information: Scan data (includes the scan data and patient number), ScanMode (type of scan performed), Analysis date, Institution or facility where scan was performed, name of operator conducting the scan, manufacturer/model of device used to perform the scan, additional comments, date report was generated;

Results File

The Result file is a JavaScript file that contains information needed to generate the table report including information identifying the number of rows and columns, title, type of table, etc.;

The Image File

The image file is a JavaScript file that contains the textual information which appears under the image in the DICOM report;

The Graph File

The Graph file contains the textual information which appears under the graph in the DICOM report;

The present invention is capable of generating a report that provides medical personal with graphics, text, numbers as well as an image on a single page or screen.

The Quantitative data can be incorporated in the Image Comments field of the file according to an embodiment of the present invention, and can be easily and efficiently retrieved programmatically. The image comments field could also contain parameter settings which control the report generation process and which could be used to customize the report generation process. These parameter settings could indicate which type of report was included in the DICOM file. Quantitative report data may also be manually input by an operator as desired.

Although the data is described as being incorporated into the Image Comments field of the DICOM file, the data could be embedded into one or more other fields in the DICOM file, including one or more other predefined proprietary fields.

The results are encoded in HTML and Java Script to accommodate graphics and images as well as numeric and text results. The HTML and Java Script components are the same ones used to generate the viewable report. A person of ordinary skill in the art will appreciate that the results can be readily retrieved and an equivalent or new report generated using the HTML and Java Script components forming the DICOM file. For example, the data in the physician's interpretative report as well as a new comprehensive report can be generated including image, graphics, text and numeric data. In addition, DICOM file including the HTML and Java Script elements can be retrieved and reformatted into an HTML web page for distribution on the Internet.

In addition, all of the raw data used by the QDR to generate the quantitative report data can be incorporated in another field of the DICOM file (e.g., the image comments field) and stored with the report. The raw data can then be subsequently retrieved with the report for reanalysis and/or for generating different types of reports.

The background level of the viewed report can be set to a value of 127 in a range of 0-255 (8-bit encoding), so that inversion of the image results in a constant background while the text changes from black to white.

A software tool can also be provided to facilitate retrieval of the embedded quantitative data, allowing the data to be more easily manipulated by less skilled programmers.

The present invention treats body composition scans (e.g., bone mineral content (BMC) scans) in a similar manner to density scans, providing a comprehensive report and an encapsulation of the quantified body composition results.

Although described above as a software system, it is of course possible to implement each of the processes in hardware, firmware or a combination of each. It will be appreciated that given the above teachings, a person skilled in the programming arts would be readily capable of implementing each of the above-described processes. The above system can be implemented on a personal computer and/or on the medical instrumentation device itself.

The present invention may be conveniently implemented using one or more conventional general purpose digital computers and/or servers programmed according to the teachings of the present specification, as will be apparent to those skilled in the computer art. Appropriate software coding can readily be prepared by skilled programmers based on the teachings of the present invention may also be implemented by the preparation of application specific integrated circuits or be interconnecting an appropriate network of conventional component circuits, as will be readily to those skilled in the art.

Numerous additional modifications and variations of the present invention are possible in view of the above-teachings. It is therefore to be understood that within the scope of the appended claims, the present invention may be practiced other than as specifically described herein.

We claim:

1. A computer executable software code stored on a computer readable medium, the code for creating a DICOM compliant file, said code comprising:
   code for creating a report, including quantitative data, from acquisition data generated by at least one of an image capture device and another form of data entry;
   code for creating a bitmap image file representing the created report;
   code for embedding the bitmap image file in an image field of a DICOM compliant file; and
   code for embedding the quantitative data in a field of the DICOM compliant file other than the image field.

2. A computer executable software code as recited in claim 1, wherein the quantitative data comprises raw data used to create the report.

3. A computer executable software code as recited in claim 1, wherein the quantitative data comprises bone mineral density (BMD) data.

4. A computer executable software code as recited in claim 1, wherein the other form of data entry includes manual entry.

5. A computer executable software code as recited in claim 1, wherein the other field comprises an Image Comments field of the DICOM file.

6. A computer executable software code as recited in claim 5, wherein data in the Image Comments Field include parameters which control a process of report generation and customization of a report.

7. A computer executable software code as recited in claim 1, wherein the quantitative data includes analysis results in computer readable form.

8. A computer executable software code as recited in claim 1, wherein the quantitative data is in a form of at least one of HTML, XML and Java Script files.

9. A method for creating a DICOM compliant file, said method comprising:
creating a report, including quantitative data, from acquisition data generated by at least one of an image capture device and another form of data entry;
creating a bitmap image file representing the created report;
embedding the bitmap image file in an image field of a DICOM compliant file; and
embedding the quantitative data in a field of the DICOM compliant file other than the image field.

10. A method as recited in claim 9, wherein the quantitative data comprises raw data used to create the report.

11. A method as recited in claim 9, wherein the quantitative data comprises bone mineral density (BMD) data.

12. A method as recited in claim 9, wherein the other form of data entry includes manual entry.

13. A method as recited in claim 9, wherein the other field comprises an Image Comments field of the DICOM file.

14. A method as recited in claim 13, wherein data in the Image Comments Field include parameters which control a process of report generation and customization of a report.

15. A method as recited in claim 9, wherein the quantitative data includes analysis results in computer readable form.

16. A method as recited in claim 9, wherein the quantitative data is in a form of at least one of HTML, XML and Java Script files.

* * * * *